United States Patent [19]

Brown

[11] Patent Number: 4,738,260
[45] Date of Patent: Apr. 19, 1988

[54] UNINTENTIONAL URINATION SENSING DEVICE

[75] Inventor: Keith A. Brown, Coos Bay, Oreg.

[73] Assignee: Travis Industries, Inc., Charleston, Oreg.

[21] Appl. No.: 724,584

[22] Filed: Apr. 18, 1985

[51] Int. Cl.[4] ...................... A61B 19/00; H01H 29/00
[52] U.S. Cl. ............................. 128/138 A; 200/61.05; 340/573; 340/604; 340/825.74; 24/306
[58] Field of Search .................... 128/138 A; 604/361; 340/573, 604, 825.74; 200/61.04, 61.05, 193; 24/306

[56] References Cited

U.S. PATENT DOCUMENTS

| | | | |
|---|---|---|---|
| 2,874,695 | 2/1954 | Vaniman | 128/138 R |
| 3,460,123 | 8/1969 | Bass | 128/138 A X |
| 3,530,855 | 9/1970 | Balding | 128/138 A |
| 3,581,208 | 5/1971 | Buehrle, Jr. et al. | 340/825.74 X |
| 3,658,107 | 4/1972 | Perina | 24/306 X |
| 3,678,928 | 7/1972 | Mozes | 128/138 A |
| 3,696,357 | 10/1972 | Kilgore | 340/573 |
| 3,809,078 | 5/1974 | Mozes | 128/138 A |
| 4,106,001 | 8/1978 | Mahoney | 340/604 |
| 4,191,950 | 3/1980 | Levin et al. | 340/604 |
| 4,205,671 | 6/1980 | Lassen | 128/138 A |
| 4,205,672 | 6/1980 | Dvorak | 128/138 A |
| 4,212,295 | 7/1980 | Snyder | 128/138 A |
| 4,430,835 | 2/1984 | Ericson | 24/306 X |

FOREIGN PATENT DOCUMENTS 2529080 12/1983 France .................... 128/138 A

OTHER PUBLICATIONS

"Instructions for the Care and Use of Nite Train'r", Nite Train-r Enterprises, Inc., Newberg, Oreg. 97132.
"Help for Bedwetting", brochure from Palco Labs, Scotts Valley, Calif. 95066.
"Eastleigh II", brochure from Electronic Monitors, Inc., Euless, Tex. 96039.
"Enuretic Alarm", brochure from Nytone Medical Products, Inc., Salt Lake City, Utah 84119.
"Bed Wetting Alarms", catalog of Sears, Roebuck and Co., Chicago, Ill. 60680, p.534.
"Bedwetting Alarm", catalog of J. C. Penney Co., Milwaukee, Wis. 53201, p. 693.

Primary Examiner—Richard T. Stouffer

[57] ABSTRACT

An apparatus for detecting unintentional urination by a user includes an elongated belt of a liquid impermeable flexible material to which a urine sensing pad is detachably mounted. An electrical circuit carried by the belt, which may include a transmitter for sending a encoded signal to a receiver at a remote location, is responsive to the detection of urine by the urine sensing pad to provide an indication of this condition. The electrical circuitry is shielded from corrosive urine by the belt assembly. In one form, the urine sensing pad is detachably mounted to the belt by a combination of hook and eye fabric and snap fittings. Also, the urine sensing pad may be enclosed by a sheath of soft liquid absorbent material. In another form, the urine sensing pad is contained within a paper envelope.

18 Claims, 2 Drawing Sheets

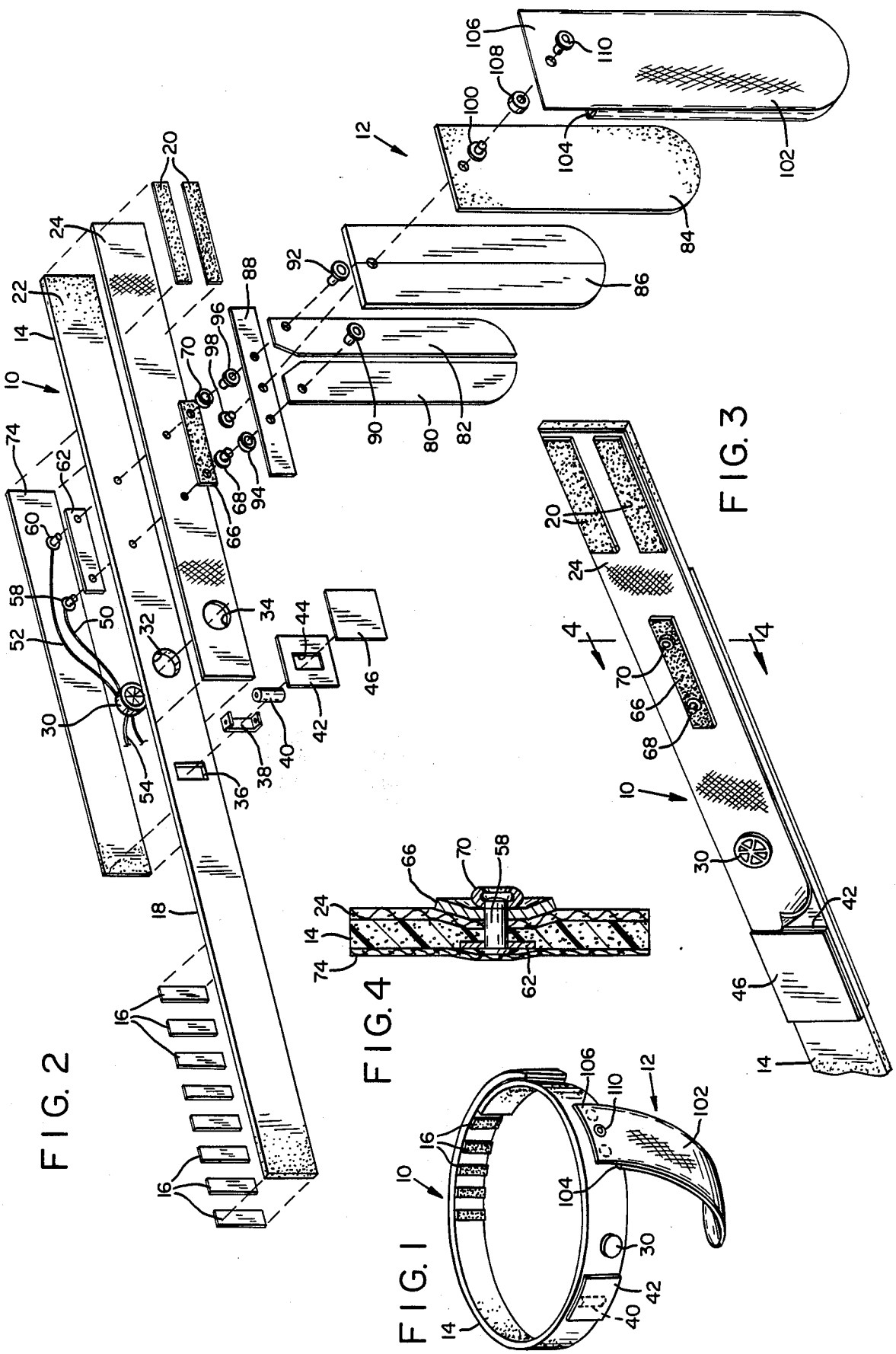

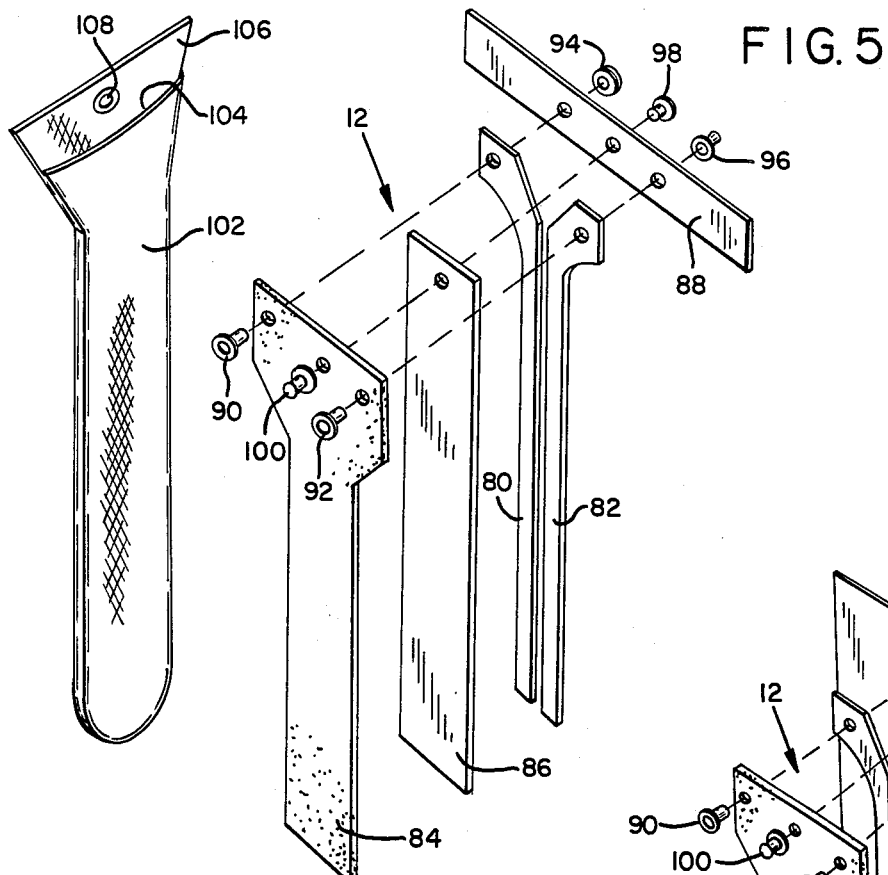
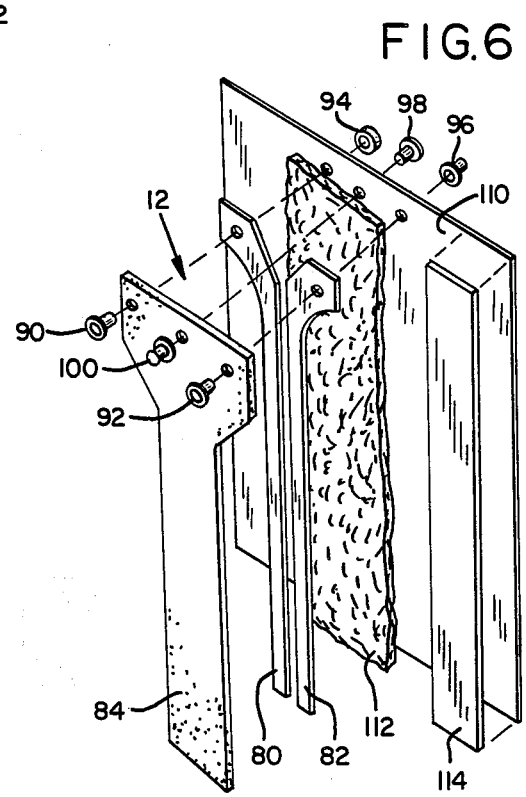
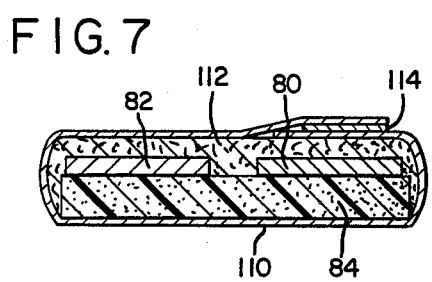
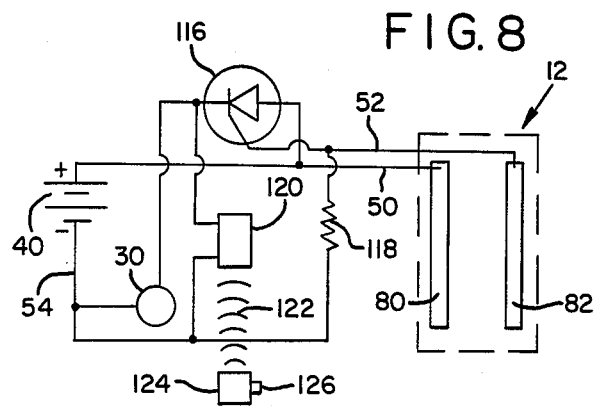
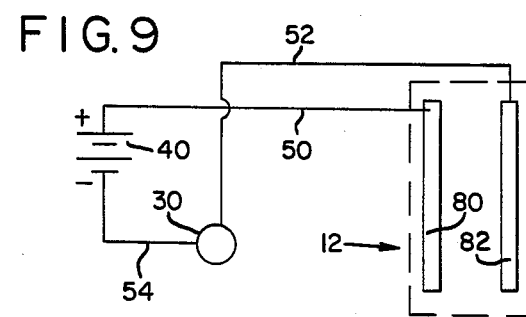

UNINTENTIONAL URINATION SENSING DEVICE

BACKGROUND OF THE INVENTION

The present invention relates to a device for detecting unintentional urination by users, such as children during the night. More particularly the invention relates to such an apparatus which has a urine sensing pad disposed adjacent the groin area of a user for detecting urine.

A number of urine sensing or anti-bed-wetting devices have heretofore been employed to train enuretic children to get up in time to empty their bladders and avoid bed-wetting.

A common early approach consisted of placing metallic grids under a bed sheet, the grids being separated by absorbent but non-conductive materials such as cotton cloth. In such devices a flow of urine into the absorbent materials completes a circuit between the grids and activates a bedside alarm after urination. In this case, the previously non-conducting dry cloth is made conductive by the urine. These devices suffered from the disadvantage of a moderate delay between the onset of urination and the sounding of an alarm. This is particularly disadvantageous because the most effective training is achieved by waking an individual immediately by an alarm upon the onset of urination and prior to the time that the individual's bladder become substantially empty. There is also the inconvenience necessitated by changes of bed linen during the night.

In the past several years, different devices have been proposed which are portable and which have an electrode containing pad disposed in the groin area of a user. A conductive path is provided between the electrodes upon urination and an alarm sounds. These devices do decrease the time between the onset of urination and the triggering of an alarm and also have the advantage of at least theoretically reducing the amount of urine flowing into the bed.

However, such prior devices have suffered from a number of disadvantages. For example, some devices have been less than completely acceptable to many children because of the bulkiness of the devices in the groin area. Also, some prior devices employ a long length of rather stiff uncomfortable electrical cord coupled from a urine sensing pad in the groin area to an alarm, such as on the wrist or shoulder of the user. Another disadvantage of some previous devices is the use of a relatively small urine sensor in the groin area of a user. Such sensors are subject to being missed by flow of urine from a user and are thereby subject to failing to trigger an alarm. Also, other prior art devices have electronic components and connectors which are exposed to highly corrosive urine.

Therefore, a need exists for an improved device for detecting unintentional urination and also for an improved urine sensing pad for such a device.

SUMMARY OF THE INVENTION

It is accordingly one object of the present invention to provide an improved apparatus for detecting unintentional urination by a user of the apparatus.

It is another object of the present invention to provide an improved urine sensing pad for detecting the presence of urine upon the pad.

Still another object of the present invention is to provide a device for detecting unintentional urination by a user which includes a belt assembly worn by the user and also includes a urine sensing pad detachably mounted to the belt so as to be readily removable from the belt while being tightly held to the belt prior to removal.

A further object of the present invention is to provide an apparatus for detecting unintentional urination by a user, the apparatus having electrical components which are shielded from highly corrosive urine.

As another aspect of the present invention, the belt is made of a comfortable synthetic material.

As a further aspect of the present invention, in one embodiment of a urine sensing pad, a combination of hook and eye fabric and snap fasteners are utilized for detachably securing the sensing pad to the belt.

As a further aspect of this particular embodiment of the sensing pad, means are provided for detachably securing a soft liquid absorbent sheath to the sensing pad and thus to the belt when the sensing pad is mounted to the belt.

As still another aspect of the present invention, the pads may be disposable and constructed of inexpensive materials.

As still another aspect of the present invention, the device includes electrical circuit means which reliably sounds an alarm upon urine reaching the sensing pad.

As a further aspect of the present invention, one form of such circuit means includes a transmitter means for sending a coded signal upon the presence of urine on the sensing pad. A receiver means at a remote location triggers an alarm upon the reception of the encoded signal from the transmitter means.

As still another aspect of the present invention, the device is relatively inexpensive to manufacture, maintenance free, portable, light weight, durable, and reliable.

These and other aspects of the present invention will become apparent with reference to the following description and drawings.

BRIEF DESCRIPTION OF THE DRAWINGS

FIG. 1 illustrates an anti-bed wetting apparatus in acordance with the present invention shown in the position it would be in when worn by a user;

FIG. 2 is an exploded view of the apparatus of FIG. 1;

FIG. 3 is a front isometric view of a portion of the apparatus of FIG. 2 in an assembled state;

FIG. 4 is a cross-sectional view of the apparatus of FIG. 3, taken along lines 4—4 in FIG. 3;

FIG. 5 is an exploded view of another form of urine sensing pad utilized in the apparatus of FIG. 1;

FIG. 6 is an exploded view of still another form of urine sensing pad utilized in the apparatus of FIG. 1;

FIG. 7 is a cross-sectional view through an assembled pad of the type shown in FIG. 6;

FIG. 8 is an electrical schematic diagram of one form of urine indicating circuit utilized in the apparatus of FIG. 1, this circuit including a thyrister or silicon controlled rectifier and an optional transmitter for sending an encoded signal to a receiver equipped for decoding the signal and triggering an indicator to indicate the sensing of urine from a user of the apparatus; and FIG. 9 is an electrical schematic diagram of another form of urine indicating circuit utilized in the apparatus of FIG. 1.

DETAILED DESCRIPTION OF PREFERRED EMBODIMENTS

With reference to FIGS. 1 through 4, an apparatus for detecting unintentional urination by a user of the apparatus includes an elongated belt 10 to which a urine sensing pad assembly 12 is detachably secured. The belt 10 carries an electrical circuit, coupled to electrodes in the pad assembly 12 as explained below. This circuit produces an output signal, such as an alarm signal, upon the presence of urine on the pad assembly.

More specifically, the belt 10 includes an elongated body 14 of a material which is impermeable to urine, such as a closed celled synthetic foam. This foam may be a thick polyethylene material, such as from three-eighths to one-half inches thick, to provide cushioning to the user. As a result, batteries and other circuit components are surrounded by the foam. Therefore, when a user lies down with these components positioned between the user's body and a bed, the forces exerted by these components on the user's body are minimized.

The belt 10 is adjustable in length to fit various sized users. For this purpose, plural spaced apart strips 16 of hook and eye fabric, such as sold under the trademark Velcro, are secured, as by adhesive, to the inner surface 18 of the belt. Strips 16 extend transversely between the side edges of the belt. In addition, a pair of spaced apart hook and eye fabric strips 20, extending parallel to the longitudinal axis of the belt, are mounted to the outer surface 22 of the belt at the other end thereof. For reinforcing purposes, an optional nylon panel 24 is secured to the surface 22 and the strips 20 are mounted to the exterior surface of this panel. As shown in FIG. 1, the strips 20 cooperatively engage the strips 18 to secure the belt in a loop about the body of a user.

As previously mentioned, the belt carries an electrical circuit for signaling the detection of urine by the pad assembly 12. Two such circuits are illustrated in FIGS. 8 and 9 and will be described in greater detail below. However, the FIG. 9 version of the circuit is included in the illustrated FIG. 2 embodiment of the apparatus. In this embodiment, a commercially available buzzer or alarm 30 of circular cross section is included. The belt body 14 includes a circular opening 32 which is sized somewhat smaller than the cross section of the buzzer 30. For this reason, when the buzzer is inserted through opening 32, and through a corresponding opening 34 in the overlying panel 24, the portions of the belt body surrounding opening 32 are compressed and bear tightly against the buzzer. This minimizes the passage of corrosive urine between the sides of the buzzer and the portion of the belt bounding the opening 32. In addition, further sealing is accomplished by using adhesive to secure the buzzer to the belt body where the buzzer passes through opening 32.

The belt body is also provided with a rectangular opening 36 for receiving a battery holder 38 therein. A battery 40, such as a twelve volt battery, is positioned within battery holder 38 to energize the circuit. To seal the battery compartment from urine, the opening 36 is surrounded by a pad 42 of hook and eye fabric. This pad includes a cut out region 44 corresponding in size and shape to the opening 36. A cover 46 of hook and eye fabric overlies and encloses the opening 44 to effectively seal the battery compartment from urine while providing ready access to the battery simply by removing the cover. Although not liquid tight, this covering arrangement does substantially slow the seepage of liquid into the battery compartment. As a result, when a user of the apparatus accidentally wets the bed, the alarm 30 will sound and awaken the user well before the time that liquid will reach the interior of the battery compartment.

Incidentally, the buzzer 30 in the preferred embodiment is of plastic, is available from Star Micronics, and designated an RMB-12 Buzzer. This particular buzzer provides an excellent seal against the penetration of urine into the buzzer and also between the exterior and interior surfaces of the belt. The circuit also includes a conductor 50, connected at one end, as by soldering, to the positive terminal engaging portion of battery holder 38 and at its other end to an electrically conductive rivet 58. Also, a conductor 52 is connected to one terminal of the buzzer 30 and to another rivet 60. In addition, a conductor 54 is connected to another terminal of the buzzer 30 and to the negative battery terminal engaging portion of the battery holder 38.

The rivet 58 extends through a backing strip 62, the belt body 14, the panel 24, a strip 66 of hook and eye fabric and is secured in place by a male snap fitting 68. The rivet 60 extends through the strip 62, body 14, panel 24, strip 66 and is held in place by a female snap fitting 70. The body 14 is compressed by and seals the space between the rivets and portions of the body through which the rivets pass. This prevents the flow of urine past the rivets between the exterior and interior surfaces of the body. A sealing panel 74, of a liquid impermeable material such as closed celled polyethylene foam, is fastened to the belt surface 18. Panel 74 overlies and seals the electrical circuit components from urine at the interior or rear surface of the belt. The strip 66 and snap fittings 68, 70 assist in detachably securing the pad assembly 12 to the belt. In addition, the snap fittings 68, 70 make electrical contact with electrodes of the pad assembly as explained below.

One form of pad assembly 12, as shown in FIGS. 1 and 2, includes a urine sensing pad comprised of a pair of elongated spaced apart electrodes 80, 82 secured to a backing panel 84, as by double backed adhesive tape 86. The panel 84 may be of a liquid impermeable closed celled synthetic foam, such as of polyethylene. The upper end of the electrodes, tape and backing subassembly is entirely surrounded by a strip 88 of hook and eye fabric. The strip 88 may be adhesively backed for mounting to the upper end of this subassembly. A rivet 90 passes through electrode 80 and makes electrical contact therewith. Another rivet 92 passes through, and makes electrical contact with, the electrode 82. These rivets 90, 92 extend through the strip 88 and are secured in place by respective female and make snap fittings 94, 96. With this construction, the snap fittings 94, 96 engage the fittings 68, 70 and detachably secure the pad subassembly to the belt. In addition, the hook and eye fabric strip 88 cooperatively engages the hook and eye fabric strip 66 to also assist in detachably mounting the subassembly to the belt. The use of the strips 66 and 88 removes strain from the connections 68 to 94 and 70 to 96.

An additional rivet 98 extends through the strip 88, tape 86, backing 84 and is secured in place by a male snap fitting 100. A sheath 102 of a soft absorbent material, such as flannel or cotton, is provided with an opening 104 at its upper end. This sheath receives the electrode tape and backing panel subassembly therein. The sheath has an upwardly projecting flap 106 with a female fitting 108 secured by a rivet 110. Fitting 108 engages the fitting 100 to secure the subassembly within the sheath when the pad assembly 12 is completely assembled.

The pad assembly 12 shown in FIG. 2 is designed for wearing by a male user. This assembly is placed in the groin area of the user when the belt is worn. Upon urination, the sheath 102 absorbs urine to provide a conductive path between the electrodes 80 and 82. When this occurs, current flows from the battery through the conductor 50, electrode 80, the electrode 82, the conductor 52, through buzzer 30, conductor 54 and to the battery. Under these conditions, the buzzer 30 is activated and sounds an audio alarm. This alarm will awaken the user of the belt almost immediately upon the commencement of unintentional urination. Thus, the user is typically awakened before the user's bladder is empty. This enhances the effectiveness of the apparatus in training a user to avoid bed-wetting, as compared to devices which do not sound an alarm until after urination is substantially complete.

The pad assembly 12 is extremely comfortable when worn by the user. In addition, with the illustrated fastening mechanism, the pad does not tend to twist when worn. Also, because of the width of the pad, it is difficult for a user to miss the pad when unintentional urination commences. Typically, conventional underpants are worn over the pad assembly to help hold it against the user's body in the groin area.

With reference to FIG. 5, an alternate form of pad assembly 12 is illustrated. This pad assembly is narrower than the assembly shown in FIG. 2 because it is designed specifically for a female user. That is, a narrower pad is more comfortable and satisfactory for a female user than a wider pad. Because of the similarities between the embodiments of FIG. 2 and FIG. 5, corresponding elements are labeled with corresponding numbers. Thus, this embodiment of the pad assembly is easily understood with reference to the prior discussion of the pad assembly of FIG. 2.

Still another form of pad assembly is illustrated in FIG. 6. The assembly of FIG. 6 includes first and second electrodes 80, 82 and a backing panel 84. The electrodes 80, 82 in the FIG. 6 embodiment comprises adhesively backed metallic electrodes, such as of aluminum, which are mounted directly to the backing 84. The pad assembly of FIG. 6 is wrapped by an absorbent material, such as a paper envelope 110. A layer of soft absorbent material, such as a three-eighth inch thick layer of cotton 112, is positioned between the electrodes 80, 82 and the paper envelope 110. The envelope completely surrounds the pad assembly, as shown in the sectional view of FIG. 7. A strip of double backed adhesive tape 114 secures the envelope 110 in place around the assembly. In the FIG. 6 embodiment, fittings, such as snap fittings, are also utilized to secure the urine sensing pad to the belt. In addition, a snap fitting 100 is optionally provided for securing a sheath 102 in place. However, with this type of urine sensing pad, the fitting 100 and rivet 98 may be eliminated as a sheath is not typically utilized. In addition, the reinforcing strip 88 is also typically eliminated.

With this construction, the FIG. 6 embodiment of urine sensing pad is extremely inexpensive to manufacture and may simply be disposed of following use. In contrast, although the pad assembly embodiments of FIGS. 2 and 5 may also be disposed of following use, they are normally utilized several times by simply cleaning the pad assembly between wettings.

The circuit of FIG. 9 and its operation has been described above and thus will not be repeated at this time. The FIG. 8 circuit differs somewhat from the FIG. 9 circuit. In connection with FIG. 8, the conductor 52, of being coupled directly to one terminal of the buzzer 30, is instead connected to the gate of a silicone controlled rectifier or thyristor 116. The anode of thyristor 116 is connected to the conductor 50. Also, the cathode of the thyristor is connected to a terminal of the buzzer 30 which in turn is coupled via the conductor 54 to the negative terminal of the battery 40. In addition, the conductor 52 is coupled through a resistor 118 to the conductor 54. With this circuit, upon the presence of an extremely small amount of urine between the electrodes 80, 82, the thyristor 116 conducts and allows current to flow to the buzzer 30 and sound an alarm. By using a thyristor, the amount of current delivered to the buzzer 30 is not dependent upon the amount of current that flows between the electrodes 80, 82 once a threshold is reached. Therefore, a strong alarm signal is produced almost immediately when urine is present between the electrodes 80 and 82.

In addition, the circuit of FIG. 8 includes an encoder/transmitter 120 coupled between the cathode of the thyristor 116 and the negative terminal of the battery 40. When thyristor 116 conducts, current is delivered to the transmitter 120 and a coded signal, indicated by wave lines 122, is sent to a receiver unit 124. The receiver unit is typicaly located at a location which is remote from the transmitter unit 120. For example, the receiver unit 124 may be positioned in the parent's bedroom while the transmitter unit is on a belt worn by a child in another bedroom. When the receiver unit 124 detects the coded signal, an indicator 126, such as a buzzer or light, is activated. This signals the reception of the coded signal by the receiver, and thereby urination by the wearer of the belt. The transmitter 120 and receiver 124 are commerically available. For example, a National Semiconductor LM 1871 RC Encoder/Transmitter is suitable with a corresponding receiver.

With such a transmitter and receiver arrangement, a number of these anti-bed-wetting devices may be used in an apartment house or common dwelling without interfering with one another. That is, each of the devices is designed to receive and send a distinctly different coded digital signal so that the various receivers are not inadvertently activated by spurious signals from other devices, or by other interfering signals such as from citizens band radios and the like.

Having illustrated and described the principles of my invention with reference to one preferred embodiment, it should be apparent to those persons skilled in the art that such invention may be modified in arrangement and detail without departing from such principles. I claim as my invention all such modifications as come within the true spirit and scope of the following claims.

I claim:

1. An apparatus for detecting unintentional urination by a user of the apparatus comprising:
   an elongated belt;
   elongated urine sensing pad means including first and second separated electrodes which form a portion of an electrical circuit path, the conductivity of the portion of the circuit path between the electrodes increasing upon the presence of urine between the electrodes;
   attachment means for detachably securing the pad means to the belt with the pad means disposed adjacent the groin area of the user for the reception of urine from the user, the attachment means including a first section of hook and eye fabric means mounted to said belt means, a second section of hook and eye fabric means mounted to an upper end of said pad means and cooperatively engaging the first section of hook and eye fabric means to detachably secure the pad means to the belt, first and second spaced apart electrically conductive snap fastener means mounted to the belt and projecting through the first section of hook and eye fabric means, and third and fourth spaced apart electrically conductive snap fastener means mounted to an upper end portion of said pad means and each in electrical contact with respective one of the first and second electrodes, the third fastener means engaging the first fastener means and the fourth fastener means engaging the second fastener means to detachably secure the pad means to the belt; and electrical circuit means carried by the belt and coupled to the first and second fastener means such that the electrodes are coupled to said electrical circuit means when the first and second fastener means engage the respective third and fourth fastener means, said electrical circuit means comprising means for sensing and indicating the increase in conductivity between the first and second electrodes upon the presence of urine between the electrodes.

2. An apparatus according to claim 1 in which the second section of hook and eye fabric means surrounds the upper end of said pad means.

3. An apparatus according to claim 2 in which said pad means includes an outer backing panel of closed celled foam material and means for adhesively securing the first and second electrodes to a single face of the backing panel.

4. An apparatus according to claim 1 including pad sheath means of a liquid absorbing material for receiving the pad means through an upper opening in the sheath means and for surrounding the received portion of the pad means, the pad sheath means having a closed bottom and the apparatus also including sheath fastener means for detachably connecting the sheath means to the pad means.

5. An apparatus according to claim 4 in which the sheath means is of a flannel material and the pad means and sheath means have rounded lower corners.

6. An apparatus according to claim 1 in which the belt is of a urine impermeable closed celled foam material.

7. An apparatus for detachably supporting an elongated urine detecting pad with first and second elongated spaced electrodes defining a portion of an electrical current path having a conductivity which increases when urine from a user enters that portion of the path between the electrodes, comprising:

an elongated belt of a urine impermeable closed celled foam material;

attachment means mounted to the belt for detachably securing the urine detecting pad to the belt;

electrical circuit means carried by the belt for coupling to the first and second electrodes of the pad and for sensing and indicating the increase in conductivity between the first and second electrodes upon the presence of urine between the electrodes;

the belt having a front side surface which is exposed when the belt is worn by a user and a rear side surface which is positioned adjacent to the user when the belt is worn by the user, the belt also having a first battery compartment opening and a second auditory indicator receiving opening, each of the first and second openings extending through the belt from the front side surface to the rear side surface, the attachment means including electrically conductive fastener means projecting from the front surface of the belt for engaging the first and second electrodes of the pad, the electrical circuit means including an auditory indicator means positioned in the second opening for providing an audio signal upon the presence of urine between the electrodes, battery support means positioned in the first opening for receiving a battery to power the electrical circuit means, and conductor means for electrically and operatively interconnecting the battery support means, the auditory indicator means and the fastener means such that the auditory indicator means provides an audio signal upon the presence of urine between the electrodes, the conductor means being positioned along the rear side surface of the belt, and urine impermeable panel means mounted to the rear side surface of the belt and overlying the conductor means and first and second openings for sealing the conductor means and such first and second openings from urine.

8. An apparatus according to claim 7 in which the second opening is sized smaller in cross section than the cross sectional dimension of the auditory indicator means, the portion of the belt bounding the second opening being compressed by and snugly abutting the auditory indicator means upon insertion of the auditory indicator means into the second opening, the portion of the belt bounding the second opening thereby assisting in sealing the second opening against penetration of urine from the front side surface of the belt between the auditory indicator means and the portion of the belt bounding the second opening.

9. An apparatus according to claim 8 in which the auditory indicator means is adhesively secured to the portion of the belt bounding the second opening to seal the second opening against penetration of urine from the front side surface of the belt between the auditory indicator means and portion of the belt bounding the second opening.

10. An apparatus according to claim 7 including means for covering the first opening at the front side surface of the belt for preventing penetration of urine into the first opening.

11. An apparatus according to claim 10 in which said last named means comprises a cover receiving panel of hook and eye fabric which has a central opening and which is mounted to the front side surface of the belt so as to surround the first opening with the central opening of the panel overlying and leading to the first opening, and a cover of hook and eye fabric which engages the cover receiving panel to close the central opening and thereby the battery compartment.

12. An apparatus for detachably supporting an elongated urine detecting pad with first and second elongated spaced electrodes defining a portion of an electrical current path having a conductivity which increases when urine from a user enters that portion of the path between the electrodes, comprising:

an elongated belt of a urine impermeable closed celled foam material;

attachment means mounted to the belt for detachably securing the urine detecting pad to the belt;

electrical circuit means carried by the belt for coupling to the first and second electrodes of the pad and for sensing and indicating the increase in conductivity between the first and second electrodes upon the presence of urine between the electrodes; and the belt having a front side surface which is exposed when the belt is worn by a user and a rear side surface which is positioned adjacent the user when worn by the user, the belt comprising means for substantially containing and sealing the electrical current means from urine and also comprising means for cushioning the user from the electrical circuit means, the attachment means including a first hook and eye fabric urine pad engaging strip secured to the front side surface of the belt and first and second electrically conductive snap fastener means mounted to the belt and projecting through the first hook and eye fabric strip.

13. An apparatus for detachably supporting an elongated urine detecting pad with first and second elongated spaced electrodes defining a portion of an electrical current path having a conductivity which increases when urine from a user enters that portion of the path between the electrodes, said apparatus also for indicating the presence of urine between the electrodes, said apparatus comprising:

an elongated belt of a urine impermeable closed celled foam material;

attachment means mounted to the belt for detachably securing the urine detecting pad to the belt;

electrical circuit means carried by the belt for coupling to the first and second electrodes of the pad and for sensing and indicating the increase in conductivity between the first and second electrodes upon the presence of urine between the electrodes; and the electrical circuit means including transmitter means for transmitting an encoded digital urine indicting signal upon the presence of urine between the electrodes, the apparatus also including receiver means at a location remote from the belt for receiving the encoded digital signal and producing an output signal in response to the encoded signal, the output signal for indicating the presence of urine between the electrodes.

14. A urine responsive pad for detection of unintentional urination by a user wearing the pad in combination with an electrically activated signaling apparatus comprising:

an elongated backing panel of a urine impermeable material;

first and second spaced apart electrodes mounted to the backing panel;

a liquid absorbing pad overlying the electrodes with the electrodes positioned between the pad and the backing panel;

a paper envelope surrounding the backing panel, electrodes and pad; and first and second electrode contactor means, each in electrical contact with a respective one of the electrodes and each exposed at the exterior of the pad, the electrode contactor means connecting the backing panel and electrodes to the paper envelope.

15. A pad according to claim 14 in which the first and second electrode contactor means comprise first and second snap fastener means each extending through one end portion of the pad and engaging a respective one of the first and second electrodes.

16. A pad according to claim 15 in which the backing panel is of a closed celled foam material.

17. A urine responsive pad for detection of unintentional urination by a user wearing the pad in combination with an electrically activated signaling apparatus comprising:

an elongated backing panel of a urine impermeable material;

first and second spaced apart electrodes mounted to the backing panel to form a backing panel and electrode assembly;

a hook and eye fabric reinforcing strip mounted to and surrounding one end of the backing panel and electrode assembly;

first and second electrode contactor means extending through the reinforcing strip and contacting the respective first and second electrodes.

18. A pad according to claim 17 in which the first and second electrode contactor means comprise respective first and second snap fittings, the pad including a third snap fitting and a flannel sheath for receiving the backing panel and electrode assembly, the flannel sheath being closed at the bottom and including a fourth snap fitting for engaging the third snap fitting to detachably secure the sheath to the backing panel and electrode assembly.

* * * * *